United States Patent [19]

van Waalwijk van Doorn et al.

[11] Patent Number: 4,679,546
[45] Date of Patent: Jul. 14, 1987

[54] IMPLANTABLE SHUT-OFF DEVICE

[75] Inventors: Ernst S. C. van Waalwijk van Doorn, Wijchen; Joseph D. M. de Vries, Malden; Franciscus J. M. de Vries, Wassenaar, all of Netherlands

[73] Assignee: Applied Medical Technics B.V., Wijchen, Netherlands

[21] Appl. No.: 788,155

[22] Filed: Oct. 16, 1985

[30] Foreign Application Priority Data

Oct. 17, 1984 [NL] Netherlands .................. 8403174

[51] Int. Cl.⁴ ..................... A61F 1/00; A61M 25/00
[52] U.S. Cl. ............................ 128/1 R; 128/DIG. 25; 604/9; 623/2
[58] Field of Search ............ 128/1 R, DIG. 25; 251/65; 137/454.2; 285/9.1; 604/9–10; 623/2

[56] References Cited

U.S. PATENT DOCUMENTS

| 3,181,895 | 5/1965 | Cator | 285/9.1 X |
| 3,503,400 | 3/1970 | Osthagen et al. | 128/DIG. 25 |
| 3,768,102 | 10/1973 | Kwan-Gett et al. | 128/DIG. 25 |
| 3,812,841 | 5/1974 | Isaacson | 128/1 R |
| 3,997,923 | 12/1976 | Possis | 623/2 |
| 4,574,833 | 3/1986 | Custer | 251/65 X |

FOREIGN PATENT DOCUMENTS

| 941759 | 4/1956 | Fed. Rep. of Germany . |
| 1911649 | 9/1970 | Fed. Rep. of Germany . |
| 2624418 | 12/1977 | Fed. Rep. of Germany . |

Primary Examiner—Dalton L. Truluck
Attorney, Agent, or Firm—Birch, Stewart, Kolasch & Birch

[57] ABSTRACT

A shut-off device particularly suitable for implantations in the urethra provided with a tubular housing having attaching means for permanent fitting on the wall tissue of the urethra, a valve system for closing off and making free the passage in said housing and means for disconnectably coupling said valve system in said housing, said valve system consisting of a cylindrical element wherein are arranged a valve seat having a valve co-operating therewith and magnetical means for pressing said valve and seat against one another, whereby the opening pressure can be determined by exerting downward pressure or by having the patient apply manual pressure to the abdominal wall.

10 Claims, 5 Drawing Figures

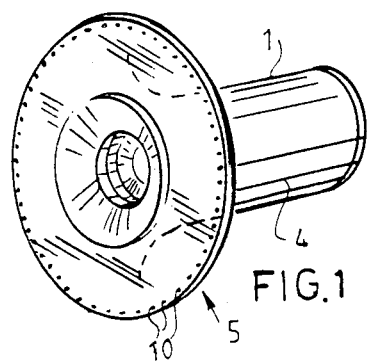
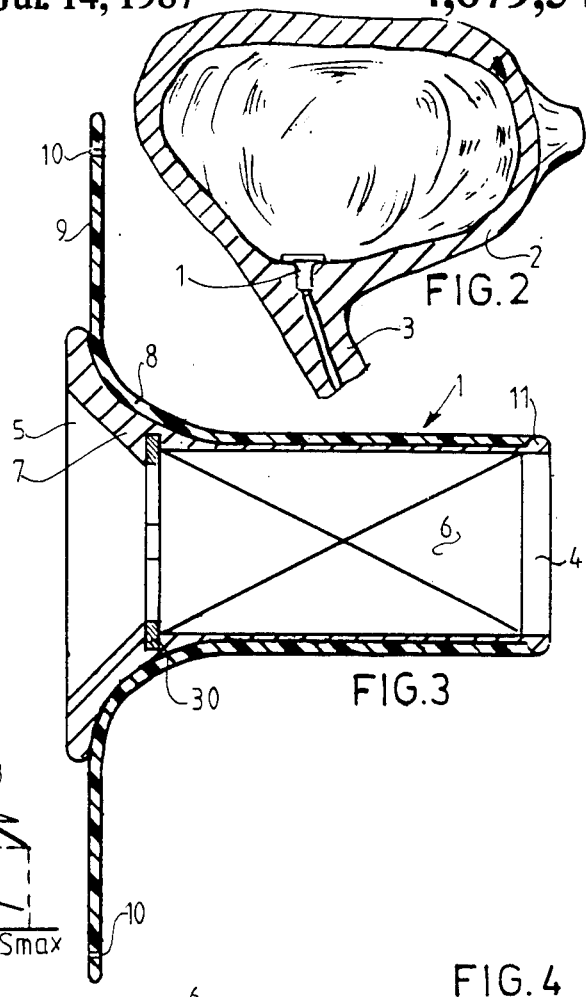
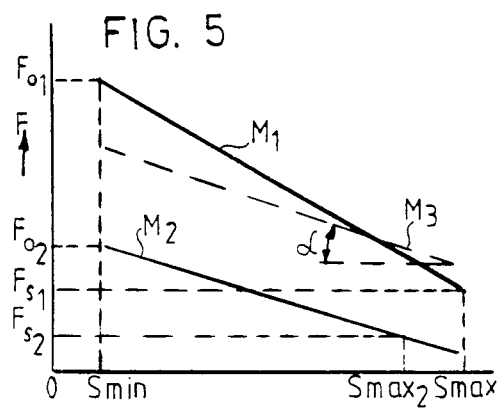

IMPLANTABLE SHUT-OFF DEVICE

The invention relates to a shut-off device particularly suitable for implantations in the urethra. The invention has for its object to make such a shut-off device operable as naturally as possible, i.e. that at a predetermined pressure in the urine bladder of the patient the device opens, allows sufficient through-flow and subsequently closes again. The opening pressure can be determined by exerting downward pressure or by having the patient apply manual pressure to the abdominal wall. The patient is hereby given an acceptable and effective solution to his or her incontinence problem.

The shut-off device is distinguished by a tubular housing having attaching means for permanent fitting on the wall tissue of the urethra, a valve system for closing off and making free the passage in said housing and means for disconnectably coupling said valve system in said housing.

Owing to the application of the housing with permanent attachment and the disconnectable valve system, it is possible to lay the foundation for the valve system proper with a relatively minor operation, and in subsequent replacement of said valve system to remove same from or place it in said housing using a catheter/endoscope. As a result, subsequent operations become unnecessary.

In one embodiment, the valve system consists of a cylindrical element wherein are arranged a valve seat having a valve co-operating therewith and spring means for pressing said valve and seat against one another. Said means are preferably given a magnetic form, whereby said valve acquires a force-path curve that is favourable for this purpose. Said means are further made adjustable in order to be able to vary the opening pressure depending on the patient data.

In a preferred embodiment the housing features a funnel-shaped form besides a cylindrical part. Said funnel form is highly suitable for implantation at the junction between the bladder and urethra, whereby the funnel-shaped part opens out into the bladder.

According to the invention the housing is coated on its exterior with a layer of tissue compatible bonding material. This material does not cause any rejection symptoms but on the contrary is suitable for growth of the tissue.

In order to make possible continual fitting or removal of the valve system in the implanted housing, the latter is provided on the end turned away from the funnel with a wall thickening, the outside surface of which runs flush with that of the layer of bonding material. As a result this part remains free of growing tissue and said valve system can be respectively fed into and taken out of said housing without problem.

Mentioned and other characteristics of the invention will be made further apparent in the following figure description of an embodiment.

In the drawing:

FIG. 1 shows a perspective view of a device according to the invention,

FIG. 2 shows a schematic section of a bladder with urethra and device implanted therein, FIG. 3 shows an axial section of the device in FIG. 1, wherein the valve system in the housing is illustrated schematically, FIG. 4 shows an axial section of the valve system applicable in the device from FIG. 1 and 2, on a larger scale, FIG. 5 shows a diagram wherein the opening force is plotted in relation to the opening path of the valve system.

In the figures the housing of the device is indicated with the number 1, which housing, as will be apparent from FIG. 2, is suitable for implantation at the junction between the bladder 2 and the urethra 3. For this purpose said housing is formed with a cylindrical part 4 which is situated in the urethra 3 and a funnel-shaped part 5 which opens into the bladder. A valve system 6, which is further explained below, is accomodated in said cylindrical part 4.

The housing 1 consists of a rigid body of titanium alloy 7 which is coated on the exterior with a layer of tissue compatible material 8 known under the trade name "Proplast". This material bonds well to the tissue and because of its structure is suitable for making possible the growth of tissue thereon. For the attachment that is carried out once during the first operation, the layer 8 is extended on the funnel side past the inner titanium wall 7 to a bonding flange 9 which is provided with holes 10 for feeding through cord-form, stitching material suitable for this purpose.

On the other end of housing 1 said titanium inner wall 7 is thickened at 11, such that its outer surface runs flush with the outer surface of layer 8. On the one hand displacement between the two parts 7 and 8 is hereby prevented, while on the other hand tissue growth at this location is prevented, in order to enable the introduction of valve system 6 into this cylindrical end part.

An embodiment of the valve system 6 is further shown on a larger scale in FIG. 4.

Said valve system consists substantially of a cylindrical part 12, the outer circumference of which is accomodated slidably fitting in cylindrical part 4 of housing 1. Said cylindrical part 12 is formed on the inside with a bore 13, in the bottom of which a ring-shaped magnetic body 14 is attached. Said cylindrical part 12 is likewise provided at its other end with a bore 15, wherein a valve body is accomodated. By means of a screw thread or the like a ring 18 containing the valve seat 17 is screwed onto said other end.

On the left hand side in FIG. 4 the valve 16 is a truncated cone shape, the cone mantle thereof co-operating with a conical face of valve seat 17, such that a liquid tight closure is assured.

The valve 16 is screwed onto a valve carrier 19 whereby a ring 20 having radially projecting plates 21 is clamped firmly between said valve carrier 19 and the valve body 16. Said plates 21 have a circumscribed circle which corresponds with the circular inner wall of bore 15, so that said plates 21 enable axial sliding of valve body 16 in said bore 15 away from and towards valve seat 17.

At a distance from valve body 16 the carrier 19 is formed with an annular magnet 22 which co-operates with magnet ring 14 in cylindrical part 12. Said magnet rings each have conical end faces 23, 24 which run parallel to one another.

The carrier 19 is formed with an axially directed threaded hole 25, wherein a threaded body 26 is adjustable in an axial sense by rotation. Rotation is carried out by way of a slot 27 arranged in the end face of said threaded body 26, in which slot a screwdriver can be placed. The location of threaded hole 25 in relation to permanent magnet rings 14 and 22 respectively is such that said threaded body can be fed through the rings more or less whereby the path of lines of force and therefor the force of attracton of said magnet rings in relation to one another can be varied.

Finally the carrier 19 features a bush-shaped end 28 on the outside of which ribs 29 are arranged, the circumscribed circle of which corresponds with the inner surface of the bore 13. In this way accurate centric displacement of said carrier 19 in axial sense is assured. The plates 21 as well as the ribs 29 can moreover feature a blade form, so that with liquid transport in FIG. 4 from left to right through the cylindrical part 12 a rotation of the valve 16 and valve carrier 19 is brought about.

The attachment of valve system 6 in cylindrical part 4 of housing 1 can take place by means of magnets. To this end the valve casing close to the funnel-shaped end is provided with a crown of permanent magnets 30, against which a ring of magnetizable material 31 attached to the part 18 can be pressed. For fitting or removal of the valve system 6, the latter only has to be fed axially into the cylindrical part 4 of housing 1 until the ring 31 makes contact with the crown of magnets 30. Conversely the valve system 6 can be removed by being pulled loose. A safety precaution is moreover hereby achieved, if the passage of liquid is prevented when valve body 16 jams. At a sufficiently high pressure in the bladder said valve system 6 will shoot loose whereby the passage through housing 1 is left clear.

The operation of valve system 6 is as follows:

In FIG. 4 valve body 16 is drawn in the opened position and magnet rings 14, 22 are at a distance from one another. If no liquid transport is taking place the force of said magnet rings will be such that said valve body is moved to the left in FIG. 4 against valve seat 17, whereby the passage is closed off.

At a sufficiently high pressure said valve body 16 is moved to the right by the liquid which can flow away via bore 15 or 13.

The opening pressure is determined here by the extent to which the threaded body 26 is screwed into the carrier 19. As this body is carried more between the rings 14, 22, more lines of flux will be directed via said body, whereby the magnet force is increased. If however said body 26 is screwed outwards, the magnetic force of attraction is then lowered.

Secondly the opening force can be determined by the remaining clearance between magnet rings 14, 22 in the closed position of valve 16. This is determined by the difference in distance between the conical end face of valve body and magnet ring 22 less the distance between valve seat 17 and magnet ring 14. This distance is adjustable, among other ways, by changing the thickness of the ring 20 between valve body and valve carrier. By choosing a greater gap between the magnet rings 14, 22, the opening force becomes smaller.

The closing force of the magnetic rings can also be determined by limiting the movement directed in FIG. 4 towards the right of valve body 16 and carrier 19, which movement is limited by the plate-form blades 21 of ring 20 which stop against the converging part of the bore 15. By chamfering said blades more or less at A, the maximum gap size between magnet rings 14, 22 and thereby the closing force, can be accurately determined.

FIG. 5 shows the result of this graphically. The force of attraction between magnet rings 14, 22 is indicated on the vertical axis while the size of the gap between them is plotted on the horizontal axis.

The line $M_1$ shows a curve for a situation where for example the core 26 is screwed as far as possible between the rings. Line $M_2$ shows a curve whereby the threaded body 26 is unscrewed as far as possible. It will be evident that any line between these two can be obtained by determining the position of threaded body 26. Assuming that there is a minimum determined gap (Sm) present between the rings, each curve determines its own force Fo. The closing force Fs is determined by the maximum gap Smax and the corresponding curve.

It will be apparent that the curve itself can still be altered by respectively the choice of material for the magnet rings and the dimensioning thereof. The curve is likewise determined by the verical angle of the conical mantle of the respective rings 14 and 22, which angle, with a smaller value, causes a smaller angle of inclination α of the force/gap curve, see the broken line $M_3$ in FIG. 5.

The invention is not limited to the embodiment described above. Another closing means for the valve 16 can be applied instead of magnets, for example springs or the like. Within the framework of the magnetic embodiment it will be evident that the valve body and the position of the magnets relative to one another can also be different.

What is claimed is:

1. Shut off device particularly suitable for implantation in a urethra comprising a tubular housing having attachment means for permanent fitting on the wall tissue of said urethra, a valve system located in said tubular housing for respectively closing off and leaving clear the passage in said housing, means for disconnectably coupling said valve system to said housing, and said valve system consists of a cylindrical body having a valve seat, a valve co-operating therewith and means for pressing said valve and said seat against one another.

2. Shut-off device particularly suitable for implantation in a urethra comprising a tubular housing having attachment means for permanent fitting on the wall tissue of said urethra, a valve system located in said tubular housing for respectively closing off and leaving clear the passage in said housing, means for disconnectably coupling said valve system to said housing, said valve system consists of a cylindrical body having a valve seat, a valve co-operating therewith and means for pressing said valve and said seat against one another, and said pressing means are magnetically adjustable.

3. Device as claimed in claim 2, wherein said pressing means includes a first ring magnet carried by said value which co-operates with a second ring magnet firmly attached in said cylindrical body.

4. Device as claimed in claim 3, wherein said ring magnets each have a conically tapering end face.

5. Device as claimed in claim 3, wherein said first magnet ring has a core adjustable relative thereto.

6. Device as claimed in claim 1, wherein said housing has a funnel-shaped portion and a cylindrical part.

7. Device as claimed in claim 6, wherein said attachment means is provided by a layer of tissue compatible bonding material coated on said housing.

8. Device as claimed in claim 7, wherein said layer continues as a bonding flange at the wide end part of said funnel-shaped portion.

9. Device as claimed in claim 7, wherein said housing has at the end opposite from said funnel-shaped portion a wall thickening, the outer surface whereof runs flush with that of said layer of bonding material.

10. Shut-off device particularly suitable for implantation in a urethra comprising a tubular housing having attachment means for permanent fitting on the wall tissue of said urethra, a valve system located in said tubular housing for respectively closing off and leaving clear the passage in said housing, means for disconnectably coupling said valve system to said housing, and said coupling means are formed by a magnetic crown and a ring of magnetizable material co-operating therewith.

* * * * *